(12) United States Patent
Evans et al.

(10) Patent No.: US 8,512,295 B2
(45) Date of Patent: Aug. 20, 2013

(54) RIGID NEEDLE SHIELD

(75) Inventors: Christopher Evans, Long Valley, NJ (US); Brian Costello, Union, NJ (US); Graham Reynolds, West Chester, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 13/813,590

(22) PCT Filed: Aug. 19, 2010

(86) PCT No.: PCT/US2010/045975
§ 371 (c)(1),
(2), (4) Date: Jan. 31, 2013

(87) PCT Pub. No.: WO2012/023938
PCT Pub. Date: Feb. 23, 2012

(65) Prior Publication Data
US 2013/0144219 A1    Jun. 6, 2013

(51) Int. Cl.
*A61M 5/32* (2006.01)
*B65D 55/02* (2006.01)

(52) U.S. Cl.
USPC .......................................... 604/192; 215/216

(58) Field of Classification Search
USPC ................... 604/164.08, 192, 263; 215/200, 215/201, 202, 205, 211, 212, 213, 216
See application file for complete search history.

(56) References Cited

U.S. PATENT DOCUMENTS

| | | | |
|---|---|---|---|
| 1,241,536 A * | 10/1917 | Mason | ........................... 215/202 |
| 3,434,473 A | 3/1969 | Smith | |
| 3,865,236 A | 2/1975 | Rycroft | |
| 4,248,246 A | 2/1981 | Ikeda | |
| 4,300,678 A | 11/1981 | Gyure et al. | |
| 4,419,098 A | 12/1983 | Bennett | |
| 4,430,082 A | 2/1984 | Schwabacher | |
| 4,636,201 A | 1/1987 | Ambrose et al. | |

(Continued)

FOREIGN PATENT DOCUMENTS

| | | |
|---|---|---|
| EP | 0876824 A2 | 11/1998 |
| EP | 1099450 A1 | 5/2001 |

(Continued)

OTHER PUBLICATIONS

Office Action issued Feb. 6, 2013 in EP Application No. 10747130.2.

(Continued)

*Primary Examiner* — Kevin C Sirmons
*Assistant Examiner* — William Carpenter
(74) *Attorney, Agent, or Firm* — Panitch Schwarze Belisario & Nadel LLP

(57) ABSTRACT

A rigid needle shield (10) for covering a distal end of a syringe is provided. The rigid needle shield includes an elongated flexible member (20) connected to a sidewall of the rigid needle shield for moving the rigid needle shield between a first relaxed position and a second flexed position. When in the first relaxed position, the elongated flexible member is substantially within the rigid needle shield. However, when the elongated flexible member is moved to the second flexed position, the elongated flexible member extends beyond a proximal end of the rigid needle shield to engage a needle hub or a shoulder of the syringe to move the rigid needle shield distally relative to the syringe.

14 Claims, 8 Drawing Sheets

(56) References Cited

U.S. PATENT DOCUMENTS

| | | |
|---|---|---|
| 4,639,250 A | 1/1987 | Rycroft |
| 4,735,311 A | 4/1988 | Lowe et al. |
| 4,747,837 A | 5/1988 | Hauck |
| 4,758,230 A | 7/1988 | Rycroft |
| D297,570 S | 9/1988 | Ambrose et al. |
| D302,296 S | 7/1989 | Harmony |
| 4,867,746 A | 9/1989 | Dufresne |
| 4,892,521 A * | 1/1990 | Laico et al. .................. 604/192 |
| 4,964,866 A | 10/1990 | Szwarc |
| 4,981,476 A * | 1/1991 | Aichlmayr et al. ........... 604/192 |
| 4,986,818 A | 1/1991 | Imbert et al. |
| D320,277 S | 9/1991 | Gyure et al. |
| D322,671 S | 12/1991 | Szwarc |
| 5,085,647 A | 2/1992 | Henderson et al. |
| 5,085,648 A | 2/1992 | Purdy et al. |
| 5,098,400 A | 3/1992 | Crouse et al. |
| 5,120,320 A | 6/1992 | Fayngold |
| 5,131,405 A | 7/1992 | Burns |
| 5,147,325 A | 9/1992 | Mitchell et al. |
| D332,308 S | 1/1993 | Imbert et al. |
| D332,490 S | 1/1993 | Brown et al. |
| 5,192,275 A | 3/1993 | Burns |
| 5,215,528 A | 6/1993 | Purdy et al. |
| 5,222,505 A | 6/1993 | Burns |
| 5,232,455 A | 8/1993 | Hollister |
| 5,246,427 A * | 9/1993 | Sturman et al. ............... 604/192 |
| 5,250,031 A * | 10/1993 | Kaplan et al. ................ 604/110 |
| 5,250,037 A | 10/1993 | Bitdinger |
| 5,256,152 A * | 10/1993 | Marks ........................... 604/198 |
| 5,290,256 A * | 3/1994 | Weatherford et al. ........ 604/198 |
| 5,304,149 A | 4/1994 | Morigi |
| 5,308,330 A | 5/1994 | Grimard |
| 5,322,515 A | 6/1994 | Karas et al. |
| 5,328,473 A | 7/1994 | Fayngold et al. |
| 5,336,197 A | 8/1994 | Kuracina et al. |
| 5,338,310 A | 8/1994 | Lewandowski |
| 5,342,309 A | 8/1994 | Hausser |
| 5,342,320 A | 8/1994 | Cameron |
| 5,344,404 A | 9/1994 | Benson |
| 5,344,408 A | 9/1994 | Partika |
| 5,348,544 A | 9/1994 | Sweeney et al. |
| D353,456 S | 12/1994 | Fayngold et al. |
| 5,376,073 A | 12/1994 | Graves et al. |
| 5,385,555 A | 1/1995 | Hausser |
| 5,409,461 A | 4/1995 | Steinman |
| 5,423,766 A | 6/1995 | Di Cesare |
| 5,437,648 A | 8/1995 | Graves et al. |
| 5,445,619 A | 8/1995 | Burns |
| 5,462,533 A | 10/1995 | Daugherty |
| 5,466,223 A | 11/1995 | Bressler et al. |
| 5,478,316 A | 12/1995 | Bitdinger et al. |
| 5,483,973 A | 1/1996 | Benson et al. |
| 5,487,733 A | 1/1996 | Caizza et al. |
| 5,496,274 A | 3/1996 | Graves et al. |
| 5,501,675 A | 3/1996 | Erskine |
| 5,512,050 A | 4/1996 | Caizza et al. |
| 5,545,145 A | 8/1996 | Clinton et al. |
| 5,558,651 A | 9/1996 | Crawford et al. |
| 5,569,286 A | 10/1996 | Peckham et al. |
| 5,575,777 A | 11/1996 | Cover et al. |
| 5,582,597 A | 12/1996 | Brimhall et al. |
| 5,584,810 A | 12/1996 | Brimhall |
| 5,584,816 A | 12/1996 | Gyure et al. |
| 5,599,313 A | 2/1997 | Gyure et al. |
| 5,599,318 A | 2/1997 | Sweeney et al. |
| 5,601,536 A | 2/1997 | Crawford et al. |
| 5,624,402 A | 4/1997 | Imbert |
| 5,632,732 A | 5/1997 | Szabo et al. |
| D381,422 S | 7/1997 | Erskine et al. |
| 5,647,849 A | 7/1997 | Kalin |
| 5,658,254 A | 8/1997 | Reichenbach et al. |
| D383,538 S | 9/1997 | Erskine et al. |
| 5,662,617 A | 9/1997 | Odell et al. |
| 5,665,075 A | 9/1997 | Gyure et al. |
| 5,669,889 A | 9/1997 | Gyure et al. |
| 5,672,161 A | 9/1997 | Allen et al. |
| 5,674,203 A | 10/1997 | Lewandowski |
| 5,676,658 A | 10/1997 | Erskine |
| 5,681,295 A | 10/1997 | Gyure et al. |
| 5,690,619 A | 11/1997 | Erskine |
| 5,695,474 A | 12/1997 | Daugherty |
| 5,697,908 A | 12/1997 | Imbert et al. |
| 5,700,250 A | 12/1997 | Erskine |
| 5,702,367 A | 12/1997 | Cover et al. |
| 5,704,920 A | 1/1998 | Gyure |
| 5,718,239 A | 2/1998 | Newby et al. |
| 5,733,264 A | 3/1998 | Flowers |
| 5,733,265 A | 3/1998 | Bachman et al. |
| 5,735,823 A | 4/1998 | Berger |
| 5,735,827 A | 4/1998 | Adwers et al. |
| 5,738,665 A | 4/1998 | Caizza et al. |
| 5,746,726 A | 5/1998 | Sweeney et al. |
| 5,746,727 A | 5/1998 | Graves et al. |
| 5,746,733 A | 5/1998 | Capaccio et al. |
| 5,772,636 A | 6/1998 | Brimhall et al. |
| 5,792,122 A | 8/1998 | Brimhall et al. |
| 5,795,339 A | 8/1998 | Erskine |
| 5,797,880 A | 8/1998 | Erskine |
| 5,807,374 A | 9/1998 | Caizza et al. |
| 5,820,621 A | 10/1998 | Yale et al. |
| 5,824,001 A | 10/1998 | Erskine |
| 5,830,190 A | 11/1998 | Howell |
| 5,832,971 A | 11/1998 | Yale et al. |
| 5,858,008 A | 1/1999 | Capaccio |
| 5,860,962 A | 1/1999 | Lewandowski et al. |
| 5,865,806 A | 2/1999 | Howell |
| 5,868,716 A | 2/1999 | Sweeney et al. |
| 5,879,334 A | 3/1999 | Brimhall |
| 5,887,633 A | 3/1999 | Yale et al. |
| 5,891,103 A | 4/1999 | Burns |
| 5,893,842 A | 4/1999 | Imbert |
| 5,893,845 A | 4/1999 | Newby et al. |
| 5,910,130 A | 6/1999 | Caizza et al. |
| 5,911,705 A | 6/1999 | Howell |
| 5,913,846 A | 6/1999 | Szabo |
| 5,919,165 A | 7/1999 | Benson |
| 5,919,182 A | 7/1999 | Avallone |
| 5,925,020 A | 7/1999 | Nestell |
| 5,928,215 A | 7/1999 | Caizza et al. |
| 5,931,817 A | 8/1999 | Nguyen et al. |
| 5,941,857 A | 8/1999 | Nguyen et al. |
| 5,944,700 A | 8/1999 | Nguyen et al. |
| 5,947,933 A | 9/1999 | Reichenbach et al. |
| 5,951,515 A | 9/1999 | Osterlind |
| 5,951,523 A | 9/1999 | Osterlind et al. |
| 5,957,887 A | 9/1999 | Osterlind et al. |
| 5,980,493 A | 11/1999 | Smith et al. |
| 5,980,495 A | 11/1999 | Heinz et al. |
| 5,989,229 A | 11/1999 | Chiappetta |
| 6,004,294 A | 12/1999 | Brimhall et al. |
| 6,004,296 A | 12/1999 | Jansen et al. |
| 6,036,674 A | 3/2000 | Caizza et al. |
| D422,700 S | 4/2000 | Crawford et al. |
| 6,086,563 A | 7/2000 | Moulton et al. |
| 6,086,568 A | 7/2000 | Caizza |
| 6,090,078 A | 7/2000 | Erskine |
| 6,120,482 A | 9/2000 | Szabo |
| 6,183,440 B1 | 2/2001 | Bell |
| 6,186,980 B1 | 2/2001 | Brunel |
| 6,193,696 B1 | 2/2001 | Jansen et al. |
| 6,193,969 B1 | 2/2001 | Landon |
| 6,210,375 B1 | 4/2001 | Moulton et al. |
| 6,221,052 B1 | 4/2001 | Caizza et al. |
| D442,280 S | 5/2001 | Crawford et al. |
| 6,224,569 B1 | 5/2001 | Brimhall |
| 6,234,999 B1 | 5/2001 | Wemmert et al. |
| 6,273,874 B1 | 8/2001 | Parris |
| 6,298,541 B1 | 10/2001 | Newby et al. |
| 6,319,233 B1 | 11/2001 | Jansen et al. |
| D452,003 S | 12/2001 | Niermann |
| D454,394 S | 3/2002 | Jansen |
| 6,368,303 B1 | 4/2002 | Caizza |
| 6,379,333 B1 | 4/2002 | Brimhall et al. |
| 6,409,701 B1 | 6/2002 | Cohn et al. |

| Patent | Date | Inventor |
|---|---|---|
| D460,178 S | 7/2002 | Courteix |
| 6,413,237 B1 | 7/2002 | Caizza et al. |
| 6,425,884 B1 | 7/2002 | Wemmert et al. |
| D461,557 S | 8/2002 | Courteix |
| 6,432,087 B1 | 8/2002 | Hoeck et al. |
| 6,436,086 B1 | 8/2002 | Newby et al. |
| 6,440,104 B1 | 8/2002 | Newby et al. |
| D465,846 S | 11/2002 | Hwang |
| 6,485,474 B1 | 11/2002 | Heinz et al. |
| 6,491,667 B1 | 12/2002 | Keane et al. |
| 6,494,865 B1 | 12/2002 | Alchas |
| D469,178 S | 1/2003 | Courteix |
| 6,517,516 B1 | 2/2003 | Caizza |
| 6,527,747 B2 | 3/2003 | Adams et al. |
| 6,537,259 B1 | 3/2003 | Niermann |
| 6,551,286 B1 | 4/2003 | Claessens |
| 6,558,357 B1 | 5/2003 | Hoeck |
| 6,569,123 B2 * | 5/2003 | Alchas et al. ............... 604/192 |
| 6,569,143 B2 | 5/2003 | Alchas et al. |
| D476,419 S | 6/2003 | Swenson |
| 6,582,402 B1 | 6/2003 | Erskine |
| D476,733 S | 7/2003 | Swenson et al. |
| D476,742 S | 7/2003 | Wilkinson |
| 6,585,690 B1 | 7/2003 | Hoeck et al. |
| 6,588,357 B1 | 7/2003 | Hobdy |
| 6,595,954 B1 | 7/2003 | Luther et al. |
| 6,599,268 B1 | 7/2003 | Townsend et al. |
| 6,599,269 B1 | 7/2003 | Lewandowski et al. |
| 6,616,639 B2 | 9/2003 | Gagnieux et al. |
| 6,623,461 B1 | 9/2003 | Wilkinson et al. |
| 6,626,864 B2 | 9/2003 | Jansen et al. |
| 6,629,963 B2 | 10/2003 | Prais et al. |
| 6,632,098 B1 | 10/2003 | Wong et al. |
| 6,632,198 B2 | 10/2003 | Caizza |
| 6,635,032 B2 | 10/2003 | Ward, Jr. |
| 6,638,252 B2 | 10/2003 | Moulton et al. |
| 6,638,256 B2 | 10/2003 | Jansen et al. |
| 6,645,182 B1 | 11/2003 | Szabo |
| 6,648,855 B2 | 11/2003 | Crawford et al. |
| 6,652,490 B2 | 11/2003 | Howell |
| 6,659,983 B2 | 12/2003 | Crawford et al. |
| 6,659,984 B2 | 12/2003 | Maclean Crawford et al. |
| D484,976 S | 1/2004 | Wilkinson |
| 6,673,047 B2 | 1/2004 | Crawford et al. |
| 6,679,863 B2 | 1/2004 | Bush, Jr. et al. |
| 6,679,864 B2 | 1/2004 | Gagnieux et al. |
| 6,682,510 B2 | 1/2004 | Niermann |
| 6,685,676 B2 | 2/2004 | Jansen et al. |
| 6,689,106 B2 | 2/2004 | Bush, Jr. et al. |
| 6,699,217 B2 | 3/2004 | Bennett et al. |
| 6,703,059 B2 | 3/2004 | Sigal et al. |
| 6,719,730 B2 | 4/2004 | Jansen et al. |
| 6,719,732 B2 | 4/2004 | Courteix |
| 6,726,649 B2 | 4/2004 | Swenson et al. |
| 6,730,059 B2 | 5/2004 | Caizza et al. |
| D492,404 S | 6/2004 | Prais et al. |
| 6,743,186 B2 | 6/2004 | Crawford et al. |
| 6,749,588 B1 | 6/2004 | Howell et al. |
| 6,755,804 B2 | 6/2004 | Crawford |
| 6,761,704 B2 | 7/2004 | Crawford |
| 6,773,419 B2 | 8/2004 | Crawford et al. |
| 6,776,776 B2 | 8/2004 | Alchas et al. |
| 6,776,777 B2 | 8/2004 | Barrelle |
| 6,780,169 B2 | 8/2004 | Crawford |
| D496,457 S | 9/2004 | Prais et al. |
| 6,811,547 B2 | 11/2004 | Wilkinson |
| 6,832,992 B2 | 12/2004 | Wilkinson |
| 6,837,872 B2 | 1/2005 | Crawford |
| 6,837,877 B2 | 1/2005 | Zurcher |
| 6,843,781 B2 | 1/2005 | Alchas et al. |
| 6,855,129 B2 | 2/2005 | Jensen et al. |
| 6,855,130 B2 | 2/2005 | Saulenas et al. |
| 6,881,202 B2 | 4/2005 | Coleman et al. |
| 6,905,483 B2 | 6/2005 | Newby et al. |
| 6,905,485 B2 | 6/2005 | Conway |
| 6,918,891 B2 | 7/2005 | Bressler et al. |
| 6,921,388 B2 | 7/2005 | Swenson |
| 6,926,700 B2 | 8/2005 | Bressler et al. |
| 6,932,803 B2 | 8/2005 | Newby |
| 6,936,036 B2 | 8/2005 | Wilkinson et al. |
| 6,953,448 B2 | 10/2005 | Moulton et al. |
| 6,974,423 B2 | 12/2005 | Zurcher |
| 6,984,223 B2 | 1/2006 | Newby et al. |
| 6,986,760 B2 | 1/2006 | Giambattista et al. |
| RE38,996 E | 2/2006 | Crawford et al. |
| 6,997,913 B2 | 2/2006 | Wilkinson |
| 7,001,363 B2 | 2/2006 | Ferguson et al. |
| 7,018,344 B2 | 3/2006 | Bressler et al. |
| 7,036,288 B2 | 5/2006 | Vetter et al. |
| 7,041,066 B2 | 5/2006 | Wilkinson |
| 7,041,092 B2 | 5/2006 | Barrelle |
| 7,060,055 B2 | 6/2006 | Wilkinson et al. |
| 7,083,599 B2 | 8/2006 | Alchas et al. |
| 7,094,223 B2 | 8/2006 | Brunel |
| 7,101,351 B2 | 9/2006 | Crawford et al. |
| 7,108,679 B2 | 9/2006 | Alchas |
| 7,112,190 B2 | 9/2006 | Bressler et al. |
| 7,128,726 B2 | 10/2006 | Crawford et al. |
| 7,144,388 B2 | 12/2006 | Crawford |
| 7,150,725 B2 | 12/2006 | Wilkinson |
| 7,163,526 B2 | 1/2007 | Leong et al. |
| 7,179,899 B2 | 2/2007 | Mezes et al. |
| 7,182,734 B2 | 2/2007 | Saulenas et al. |
| 7,198,618 B2 | 4/2007 | Ferguson et al. |
| 7,201,740 B2 | 4/2007 | Crawford |
| 7,207,973 B2 | 4/2007 | Barrelle |
| 7,223,258 B2 | 5/2007 | Crawford |
| 7,344,517 B2 | 3/2008 | Schiller |
| D565,732 S | 4/2008 | Pech et al. |
| 7,387,615 B2 | 6/2008 | Coelho et al. |
| 7,387,617 B2 | 6/2008 | Wittland et al. |
| 7,390,312 B2 | 6/2008 | Barrelle |
| 7,428,773 B2 | 9/2008 | Newby et al. |
| D581,046 S | 11/2008 | Sudo |
| D581,049 S | 11/2008 | Sudo |
| 7,455,661 B2 | 11/2008 | Barrelle et al. |
| 7,468,054 B2 | 12/2008 | Crawford et al. |
| 7,497,847 B2 | 3/2009 | Crawford et al. |
| 7,524,308 B2 | 4/2009 | Conway |
| 7,559,919 B2 | 7/2009 | Pech et al. |
| 7,604,613 B2 | 10/2009 | Crawford et al. |
| 7,641,636 B2 | 1/2010 | Moesli et al. |
| D612,493 S | 3/2010 | Claessens et al. |
| D627,459 S | 11/2010 | Uchida et al. |
| 2001/0004685 A1 | 6/2001 | Jansen et al. |
| 2001/0012925 A1 | 8/2001 | Alchas |
| 2001/0053886 A1 | 12/2001 | Caizza |
| 2001/0056263 A1 | 12/2001 | Alchas et al. |
| 2002/0004649 A1 | 1/2002 | Jansen et al. |
| 2002/0022803 A1 | 2/2002 | Wemmert et al. |
| 2002/0026146 A1 | 2/2002 | Jansen et al. |
| 2002/0062108 A1 | 5/2002 | Courteix |
| 2002/0068909 A1 | 6/2002 | Alchas et al. |
| 2002/0103464 A1 | 8/2002 | Crawford et al. |
| 2002/0151852 A1 | 10/2002 | Crawford et al. |
| 2002/0151853 A1 | 10/2002 | Crawford |
| 2002/0156425 A1 | 10/2002 | Crawford et al. |
| 2002/0161336 A1 | 10/2002 | Crawford et al. |
| 2002/0165498 A1 | 11/2002 | Ward |
| 2002/0188256 A1 | 12/2002 | Crawford et al. |
| 2003/0014018 A1 | 1/2003 | Giambattista et al. |
| 2003/0036731 A1 | 2/2003 | Wilkinson et al. |
| 2003/0040717 A1 | 2/2003 | Saulenas et al. |
| 2003/0050607 A1 | 3/2003 | Gagnieux et al. |
| 2003/0055381 A1 | 3/2003 | Wilkinson |
| 2003/0072715 A1 | 4/2003 | Frydman et al. |
| 2003/0078540 A1 | 4/2003 | Saulenas et al. |
| 2003/0093009 A1 | 5/2003 | Newby et al. |
| 2003/0125675 A1 | 7/2003 | Caizza et al. |
| 2003/0125676 A1 | 7/2003 | Swenson et al. |
| 2003/0125677 A1 | 7/2003 | Swenson et al. |
| 2003/0135157 A1 | 7/2003 | Saulenas et al. |
| 2003/0163096 A1 | 8/2003 | Swenson et al. |
| 2003/0165498 A1 | 9/2003 | Mezes et al. |
| 2003/0176842 A1 | 9/2003 | Wilkinson et al. |
| 2003/0181859 A1 | 9/2003 | Brunel |
| 2003/0181860 A1 | 9/2003 | Swenson |
| 2003/0181861 A1 | 9/2003 | Wilkinson |

| | | |
|---|---|---|
| 2003/0181867 A1 | 9/2003 | Bressler et al. |
| 2003/0181868 A1 | 9/2003 | Swenson |
| 2003/0181869 A1 | 9/2003 | Swenson et al. |
| 2003/0181870 A1 | 9/2003 | Bressler et al. |
| 2003/0181871 A1 | 9/2003 | Wilkinson et al. |
| 2003/0181872 A1 | 9/2003 | Newby |
| 2003/0181873 A1 | 9/2003 | Swenson |
| 2003/0181874 A1 | 9/2003 | Bressler et al. |
| 2003/0181875 A1 | 9/2003 | Bressler et al. |
| 2003/0187398 A1 | 10/2003 | Crawford |
| 2003/0187399 A1 | 10/2003 | Crawford |
| 2003/0208160 A1 | 11/2003 | Crawford |
| 2003/0208161 A1 | 11/2003 | Crawford |
| 2003/0208162 A1 | 11/2003 | Crawford |
| 2003/0208165 A1 | 11/2003 | Christensen et al. |
| 2003/0212370 A1 | 11/2003 | Barrelle |
| 2003/0212380 A1 | 11/2003 | Barrelle |
| 2003/0216687 A1 | 11/2003 | Hwang |
| 2003/0220587 A1 | 11/2003 | Swenson |
| 2003/0220614 A1 | 11/2003 | Crawford |
| 2003/0229315 A1 | 12/2003 | Leong et al. |
| 2003/0229316 A1 | 12/2003 | Hwang et al. |
| 2003/0229320 A2 | 12/2003 | Zurcher |
| 2004/0010228 A1 | 1/2004 | Swenson et al. |
| 2004/0011105 A1 | 1/2004 | Nakamura et al. |
| 2004/0015135 A1 | 1/2004 | Wilkinson |
| 2004/0024370 A1 | 2/2004 | Wilkinson et al. |
| 2004/0039340 A1 | 2/2004 | Prais et al. |
| 2004/0059302 A1 | 3/2004 | Crawford et al. |
| 2004/0087912 A1 | 5/2004 | Swenson |
| 2004/0097882 A1 | 5/2004 | DiBiasi et al. |
| 2004/0111057 A1 | 6/2004 | Wilkinson |
| 2004/0111066 A1 | 6/2004 | Prais et al. |
| 2004/0111068 A1 | 6/2004 | Swenson |
| 2004/0116859 A1 | 6/2004 | Alchas et al. |
| 2004/0133172 A1 | 7/2004 | Wilkinson |
| 2004/0138629 A1 | 7/2004 | Cipoletti et al. |
| 2004/0143195 A1 | 7/2004 | Bressler et al. |
| 2004/0162523 A1 | 8/2004 | Conway |
| 2004/0167477 A1 | 8/2004 | Wilkinson et al. |
| 2004/0178098 A1 | 9/2004 | Swenson et al. |
| 2004/0181173 A1 | 9/2004 | Wilkinson |
| 2004/0186439 A1 | 9/2004 | Crawford et al. |
| 2004/0186440 A1 | 9/2004 | Jansen et al. |
| 2004/0199113 A1 | 10/2004 | Capes et al. |
| 2004/0210196 A1 | 10/2004 | Bush, Jr. et al. |
| 2004/0210197 A1 | 10/2004 | Conway |
| 2004/0236287 A1 | 11/2004 | Swenson et al. |
| 2005/0004524 A1 | 1/2005 | Newby et al. |
| 2005/0004528 A1 | 1/2005 | Barrelle et al. |
| 2005/0004551 A1 | 1/2005 | Barrelle |
| 2005/0004552 A1 | 1/2005 | Barrelle |
| 2005/0038391 A1 | 2/2005 | Wittland et al. |
| 2005/0038392 A1 | 2/2005 | DeSalvo |
| 2005/0096596 A1 | 5/2005 | Crawford et al. |
| 2005/0096597 A1 | 5/2005 | Crawford et al. |
| 2005/0096598 A1 | 5/2005 | Crawford et al. |
| 2005/0096599 A1 | 5/2005 | Crawford et al. |
| 2005/0119627 A1 | 6/2005 | Crawford |
| 2005/0119635 A1 | 6/2005 | Crawford |
| 2005/0124944 A1 | 6/2005 | Hwang |
| 2005/0137528 A1 | 6/2005 | Wilkinson |
| 2005/0148942 A1 | 7/2005 | Newby et al. |
| 2005/0159705 A1 | 7/2005 | Crawford et al. |
| 2005/0159706 A1 | 7/2005 | Wilkinson et al. |
| 2005/0159707 A1 | 7/2005 | Schiller |
| 2005/0159709 A1 | 7/2005 | Wilkinson |
| 2005/0187493 A1 | 8/2005 | Swenson et al. |
| 2005/0197629 A1 | 9/2005 | Conway |
| 2005/0215951 A1 | 9/2005 | Saulenas et al. |
| 2005/0240161 A1 | 10/2005 | Crawford |
| 2005/0245879 A9 | 11/2005 | Crawford |
| 2005/0251092 A1 | 11/2005 | Howell et al. |
| 2005/0267412 A1 | 12/2005 | Wilkinson et al. |
| 2005/0273019 A1 | 12/2005 | Conway et al. |
| 2005/0277895 A1 | 12/2005 | Giambattista et al. |
| 2006/0052748 A1 | 3/2006 | Coelho et al. |
| 2006/0069353 A2 | 3/2006 | Barrelle et al. |
| 2006/0079847 A1 | 4/2006 | Crawford |
| 2006/0106343 A1 | 5/2006 | Alchas et al. |
| 2006/0129064 A1 | 6/2006 | Conway et al. |
| 2006/0184114 A1 | 8/2006 | Tai |
| 2006/0184135 A1 | 8/2006 | Prais et al. |
| 2006/0189933 A1 | 8/2006 | Alheidt et al. |
| 2007/0016141 A1 | 1/2007 | Salto et al. |
| 2008/0215013 A1 | 9/2008 | Felix-Faure |
| 2008/0269690 A1 | 10/2008 | Felix-Faure |
| 2009/0187150 A1 | 7/2009 | Ferland et al. |
| 2010/0076382 A1 | 3/2010 | Weston |
| 2010/0198163 A1 | 8/2010 | Bonnet |

FOREIGN PATENT DOCUMENTS

| | | |
|---|---|---|
| EP | 1208861 A1 | 5/2002 |
| EP | 1312389 A1 | 5/2003 |
| EP | 1502616 A1 | 2/2005 |
| EP | 1964587 A1 | 9/2008 |
| FR | 2118339 A5 | 7/1972 |
| FR | 7045698 | 7/1972 |
| FR | 2777787 A1 | 10/1999 |
| FR | 2816848 A1 | 5/2002 |
| GB | 2398248 A | 8/2004 |
| WO | 2006/090118 A1 | 8/2006 |
| WO | 2007141603 A2 | 12/2007 |
| WO | 2008016710 A1 | 2/2008 |

OTHER PUBLICATIONS

Int'l Search Report and Written Opinion issued Nov. 2, 2010 in Int'l Application No. PCT/US2010/045975.

Int'l Preliminary Report on Patentability issued Jul. 27, 2012 in Int'l Application No. PCT/US2010/045975.

Several photographs of Stelmi Trading International needle protecting device, admitted prior art.

West Pharmaceutical Services, "RNS Assembly with NS for CZ staked needle" engineering drawing, dated Sep. 21, 2007.

* cited by examiner

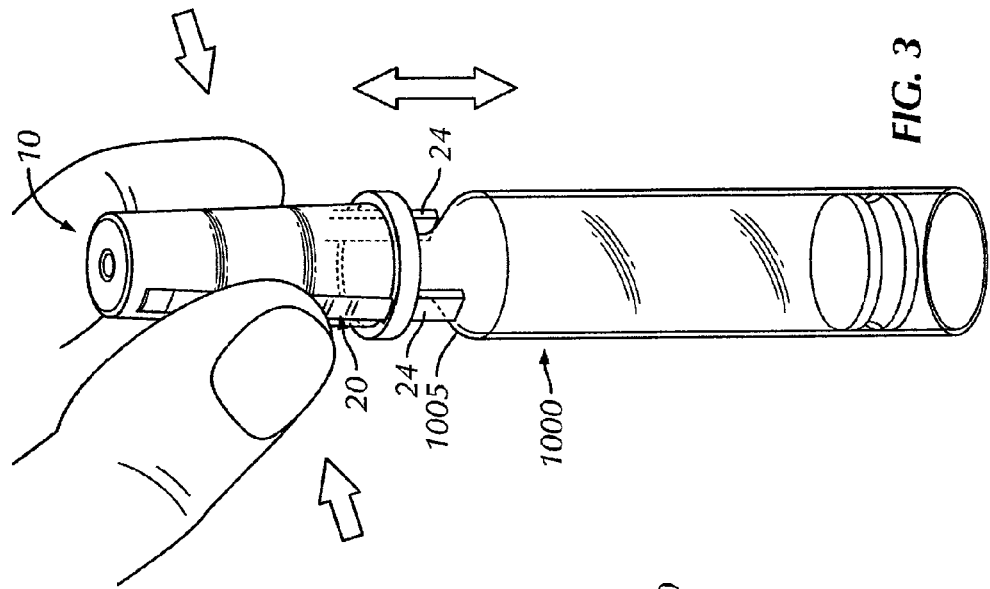
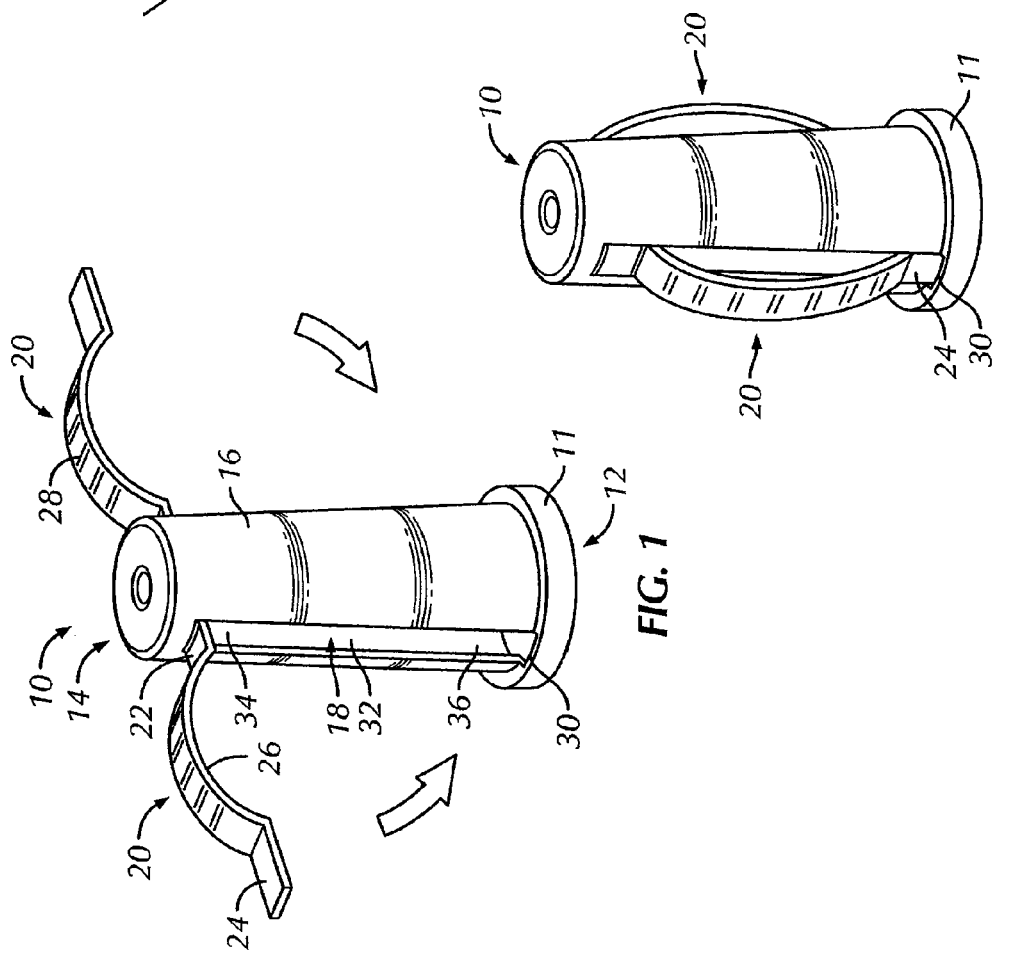

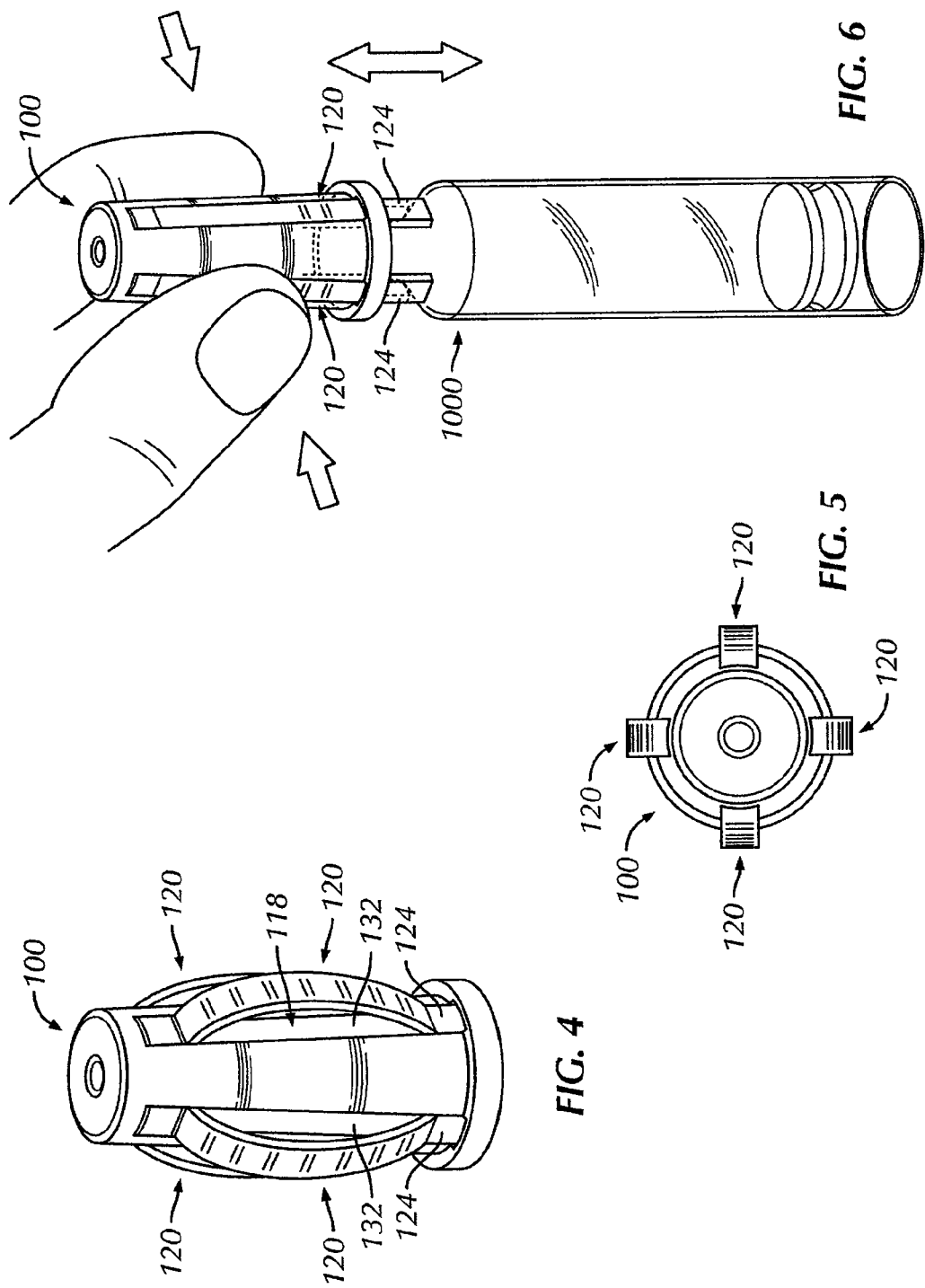

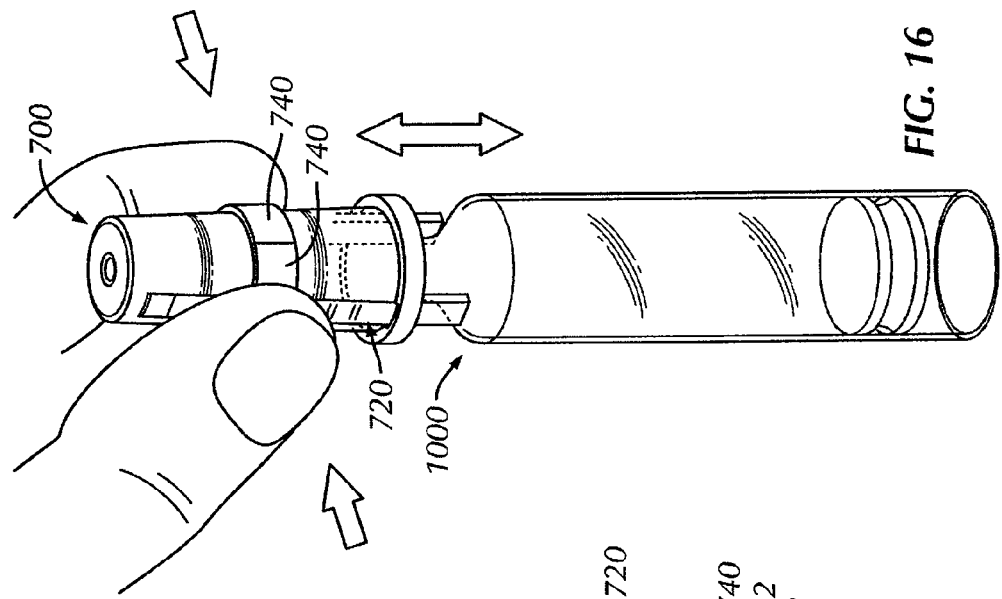
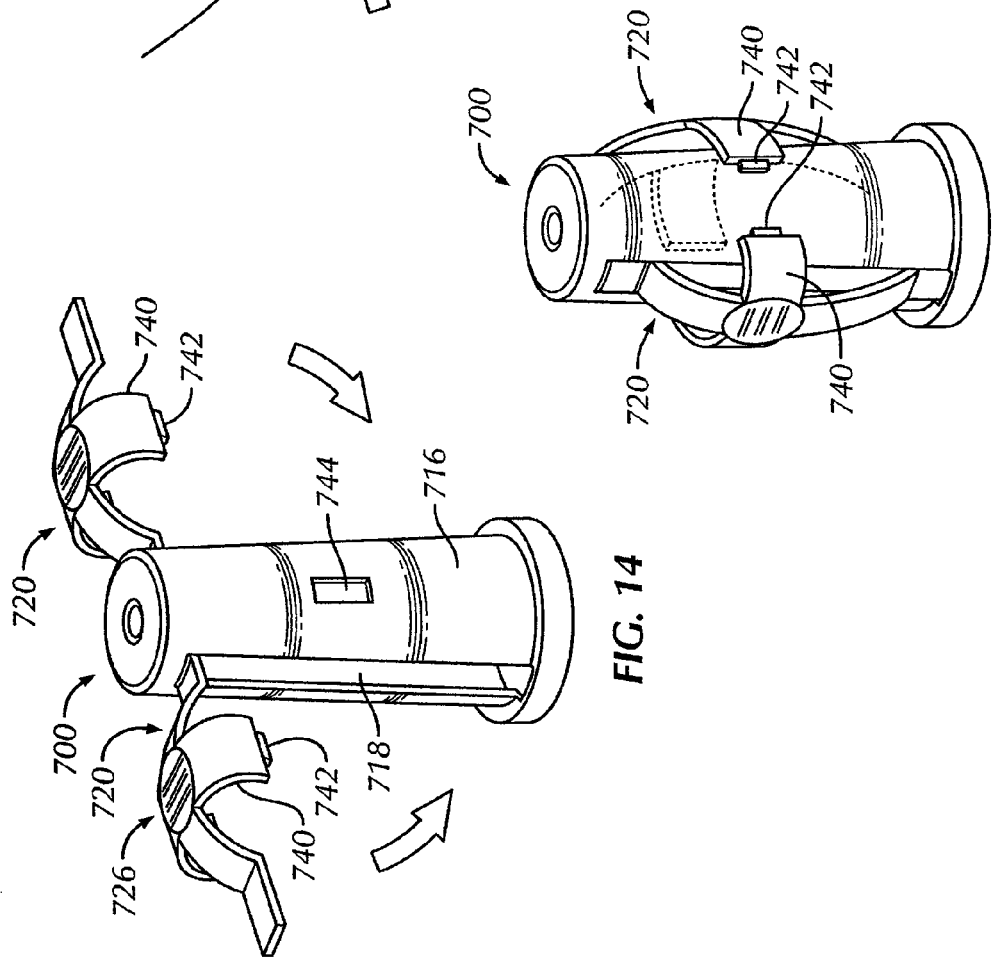

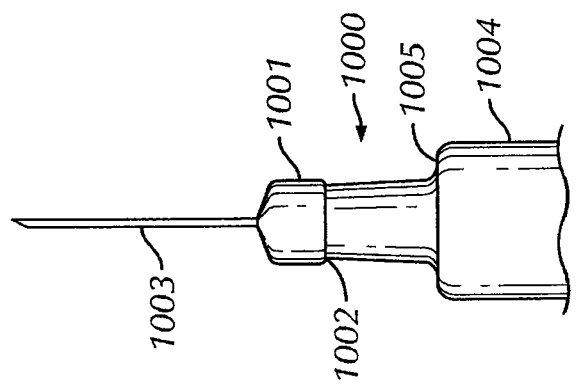
FIG. 21 (Prior Art)
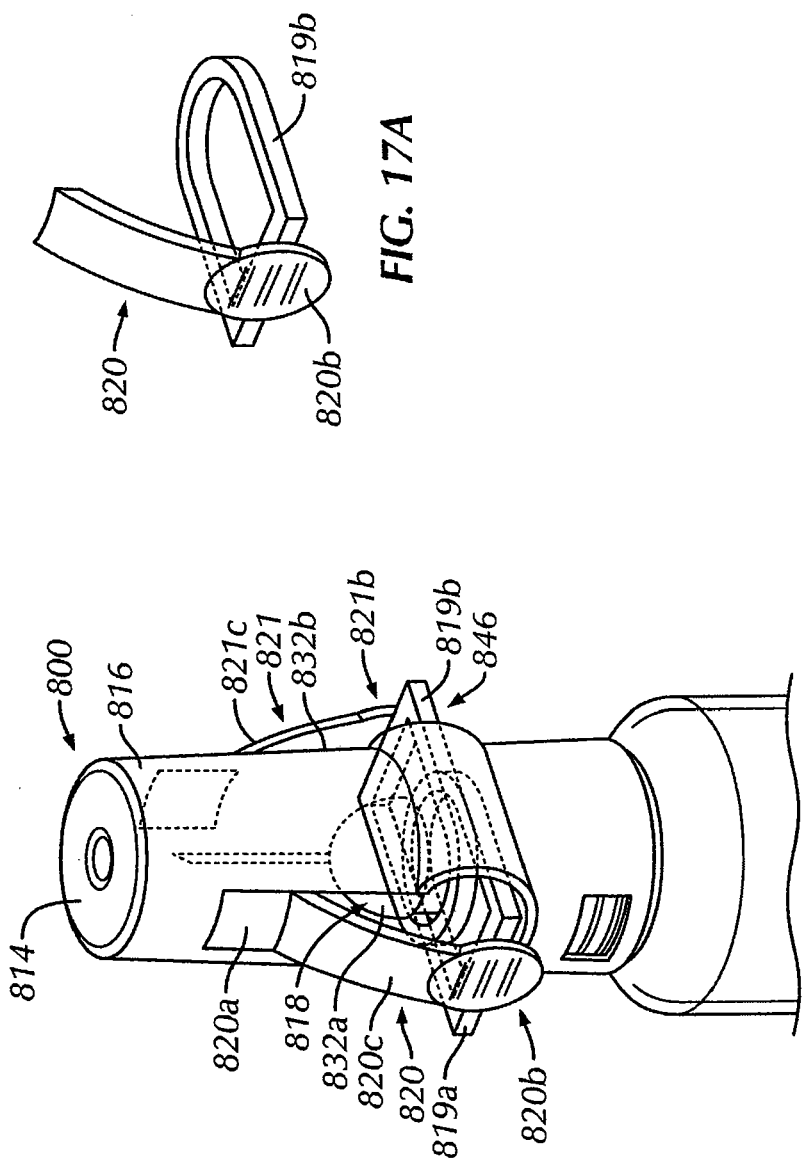
FIG. 17A
FIG. 17

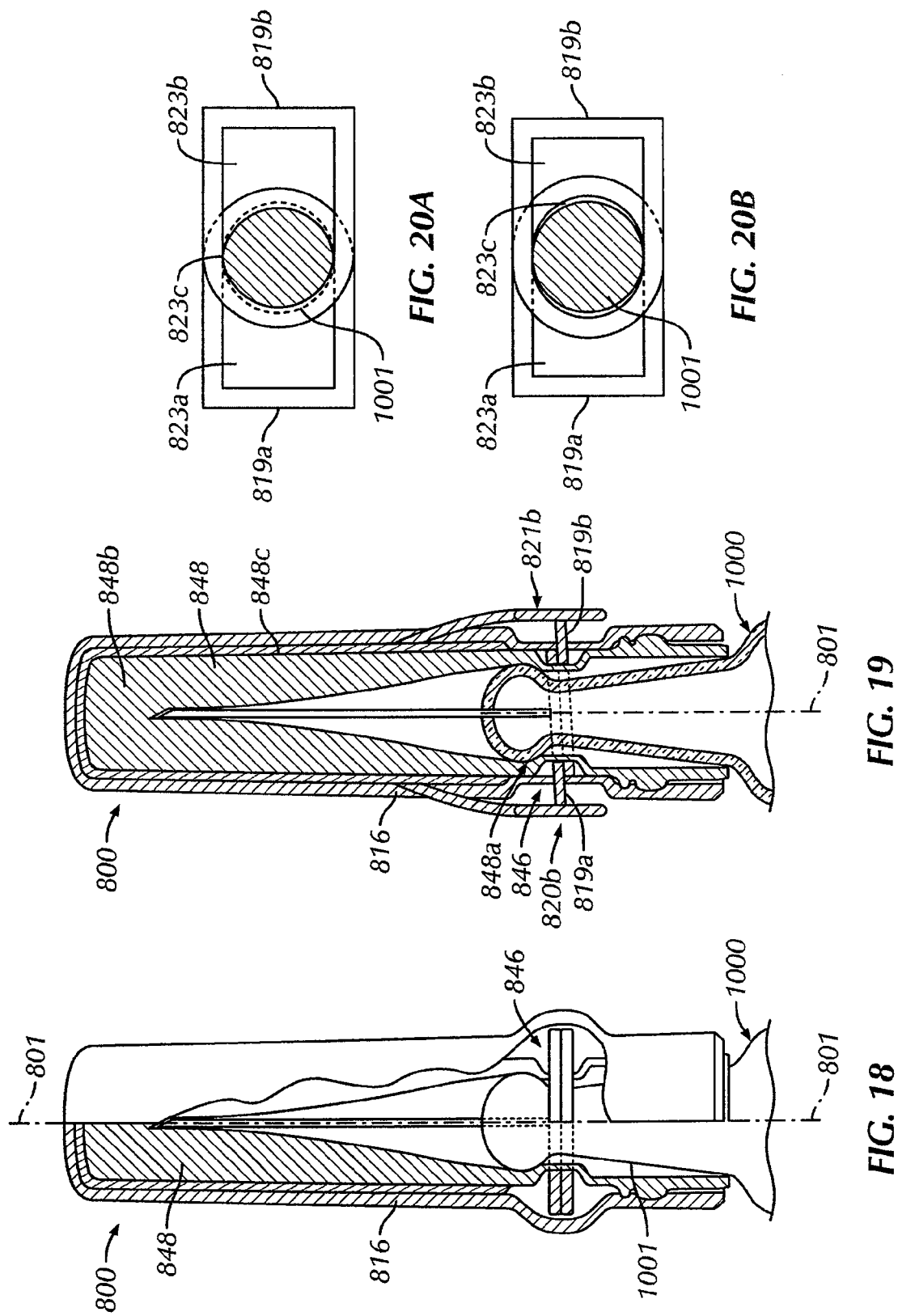

RIGID NEEDLE SHIELD

CROSS-REFERENCE TO RELATED APPLICATION

This application is a Section 371 of International Application No. PCT/US2010/045975, filed Aug. 19, 2010, which was published in the English language on Feb. 23, 2012, under International Publication No. WO 2012/023938 A1, and the disclosure of which is incorporated herein by reference.

BACKGROUND OF THE INVENTION

The present invention relates to a rigid needle shield for use with a syringe. In particular, the present invention relates to a rigid needle shield having a means to overcome the initial pull off force of the rigid needle shield from the syringe.

Removing a rigid needle shield can be major contributor to accidental needle stick injuries received in the clinical work place. This is due, in part to the phenomena of "recoil" caused when a user tries to carefully, but effectively overcome the initial pull off force required to remove a rigid needle shield from a syringe. Upon the abrupt release of the rigid needle shield from the syringe, the user compensates for the spike in initial break away force of the rigid needle shield from the syringe by pulling back slightly. Depending on reflex/reaction, the "pull back" reaction can result in the hand grasping the rigid needle shield to recoil or bounce back towards the uncovered needle in the other hand, thus resulting in an accidental needle stick injury. Accordingly, there is still a need for a rigid needle shield that addresses the foregoing problems of rigid needle shields and its potential for accidental needle stick injuries in a cost effective and economical manner.

BRIEF SUMMARY OF THE INVENTION

In accordance with a preferred embodiment, the present invention provides a rigid needle shield that includes an open proximal end, a closed distal end, a sidewall, and an elongated flexible member. The sidewall extends between the open proximal end and the closed distal end for forming an elongated chamber therebetween. The elongated flexible member is connected to the rigid needle shield and includes a first end, a second end and a middle portion. The first end is connected to the rigid needle shield. The second end is slidably connected to the rigid needle shield proximate an open proximal end. The middle portion extends between the first end and the second end. The middle portion is also deflectable to move the elongated flexible member between a first relaxed position and a second flexed position wherein the second end extends beyond the open proximal end.

In another preferred embodiment, the present invention provides a syringe assembly that includes a syringe and a rigid needle shield. The syringe includes a barrel having a shoulder, a needle hub extending from the shoulder, and a needle extending from a needle hub. The rigid needle shield is releasably connected to the needle hub for covering the needle hub and the needle. The rigid needle shield includes an open proximal end, a closed distal end, a sidewall and an elongated flexible member. The sidewall extends between the open proximal end and the closed distal end for forming a chamber therebetween. The elongated flexible member is connected to the rigid needle shield and includes a first end, a second end, and a middle portion. The first end is connected to the rigid needle shield. The second end is slidably connected to the rigid needle shield proximate the open proximal end. The middle portion extends between the first end and the second end and is deflectable to move the elongated flexible member between a first relaxed position and a second flexed position. In the first related position, the second end is substantially within the elongated chamber or proximate the open proximal end. In moving from the first relaxed position to the second flexed position, the second end extends beyond the open proximal end to engage at least one of the needle hub and shoulder to move the needle shield distally relative to the syringe.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a perspective view of a first preferred embodiment of a rigid needle shield in accordance with the present invention in an "as molded" position;

FIG. 2 is a perspective view of the rigid needle shield of FIG. 1 in a fully assembled position;

FIG. 3 is a perspective view of the rigid needle shield of FIG. 1 assembled to a syringe in a flexed position;

FIG. 4 is a perspective view of a second preferred embodiment of a rigid needle shield in accordance with the present invention;

FIG. 5 is a top plan view of the rigid needle shield of FIG. 4;

FIG. 6 is a perspective view of the rigid needle shield of FIG. 4 assembled to a syringe in a flexed position;

FIG. 14 is a perspective view of an eighth preferred embodiment of a rigid needle shield in accordance with the present invention in an "as molded" position and with a groove formed within a sidewall of the rigid needle shield;

FIG. 15 is a perspective view of the rigid needle shield of FIG. 14 in a fully assembled relaxed position without the groove of FIG. 14;

FIG. 16 is a perspective view of the rigid needle shield of FIG. 14 assembled to a syringe in a flexed position;

FIG. 17 a perspective view of a ninth preferred embodiment of a rigid needle shield in accordance with the present invention;

FIG. 17A is a greatly enlarged, perspective view of a portion of a clamp assembly of the rigid needle shield of FIG. 17;

FIG. 18 is a partial, cross-sectional, side elevational view of the rigid needle shield of FIG. 17 attached to a syringe;

FIG. 19 is a partial, cross-sectional, front elevational view of the rigid needle shield of FIG. 17 assembled to a syringe rotated 90 degrees from FIG. 18;

FIG. 20A is a schematic, top plan view of the clamp assembly of the rigid needle shield of FIG. 17 in a closed position;

FIG. 20B is a schematic, top plan view of the clamp assembly of the rigid needle shield of FIG. 17 in an open position; and FIG. 21 is a partial, elevational view of a distal end of a conventional syringe applicable for use with the present invention.

DETAILED DESCRIPTION OF THE INVENTION

Figure 8:
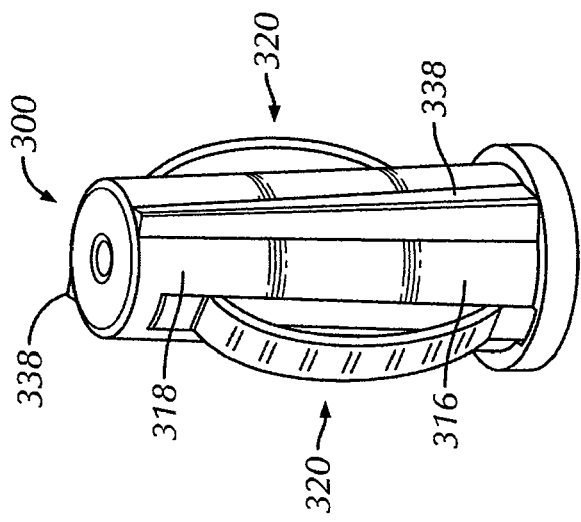
FIG. 8 is a perspective view of a fourth preferred embodiment of a rigid needle shield in accordance with the present invention.

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Unless specifically set forth herein, the terms "a," "an" and "the" are not limited to one element but instead should be read as meaning "at least one." The terminology includes the words noted above, derivatives thereof and words of similar import.

In a first preferred embodiment, the present invention provides a rigid needle shield 10, as best shown in FIGS. 1-3. The rigid needle shield is configured, as best shown in FIG. 1 and includes an open proximal end 12, a closed distal end 14, a sidewall 16 and an elongated flexible member 20. In general, the rigid needle shield 10 has a substantially tubular configuration. The sidewall 16 extends between the open proximal end 12 and the closed distal end 14 forming an elongated chamber 18. The rigid needle shield 10 also includes a radially outwardly extending rim 11 about its open proximal end 12. Preferably, the elongated chamber 18 tapers in the distal direction such that the overall outside diameter of the closed distal end 14 is smaller than the overall outside diameter of the rim 11, about the rigid needle shield's proximal end 12. In other words, the rigid needle shield 10 has a substantially frustroconical overall profile.

The elongated flexible member 20 includes a first end 22, a second end 24 and a middle portion 26 extending between the first end 22 and the second end 24. The first end 22 is connected to at least one of the closed distal end 14 and the sidewall 16 of the rigid needle shield 10. The first end 22 is preferably pivotably connected to the closed distal end 14 or the sidewall 16. More preferably, the first end 22 is connected to the sidewall 16 by a living hinge connection. The second end 24 is a free end. That is, the second end 24 is not permanently fixed or attached to any other portion of the rigid needle shield 10. In other words, the second end 24 can be slidably connected to the needle shield 10 proximate the open proximal end 12. The middle portion 26 of the elongated flexible member 20 extends between the first end 22 and the second end 24. Preferably, the middle portion 26 is convex, bowing outwardly from the sidewall 16 when in the fully assembled state, as best shown in FIG. 2. Furthermore, the middle portion 26 can optionally be configured to with ribs or grooves 28 or any alternative surface texturing about an outer surface of the middle portion 26 to facilitate gripping of the middle portion 26 by a user. The middle portion 26 is deflectable to move the elongated flexible member 20 between a first relaxed position (FIG. 2) and a second flexed position (FIG. 3). In the second flexed position, the second end 24 extends beyond the open proximal end 12.

The elongated chamber 18 includes an opening 32 formed within the sidewall 16. The opening 32 includes a distal end 34 and a proximal end 36. The opening 32 is also positioned proximate the first end 22 of the elongated flexible member 20, such that the first end 22 is connected to the rigid needle shield 10 proximate the distal end 34 of the opening 32 while the second end 24 can be substantially received within the proximal end 36 of the opening 32.

The rigid needle shield 10 can be configured with a single elongated flexible member 20 and a single opening 32. However, the rigid needle shield 10 is preferably configured with a pair of elongated flexible members 20 and a pair of openings 32 that are each diametrically opposed from each other about the rigid needle shield 10, as best shown in FIGS. 1-3. The middle portion 26 of each elongated flexible member 20 extends outwardly from the openings 32, respectively, as best shown in FIG. 2.

FIG. 2 illustrates the rigid needle shield 10 in a fully assembled and relaxed position. In the assembled position, the second end 24 of the elongated flexible member 20 resides within an inner portion 30 of the proximal end 36 of the rigid needle shield 10, e.g., an inner surface of the rim 11. In other words, the second end 24 resides substantially within the elongated chamber 18 adjacent the open proximal end 12. The fully assembled position, as shown in FIG. 2, corresponds to a first relaxed position for the elongated flexible members 20. This is also the position and configuration in which the rigid needle shield 10 is assembled to a syringe 1000 (FIG. 21). The rigid needle shield 10 can be secured to the syringe 1000 by the inclusion of a resilient needle sheath (not shown), similar to the resilient needle sheath 848 (FIG. 18) of the ninth preferred embodiment discussed below. Such resilient needle sheaths are known in the art and a detailed discussion of their operation and structure is not necessary for a complete understanding of the present invention. However, such resilient needle sheaths are configured to surround a needle (e.g., 1003) of a syringe (e.g., 1000) along with an undercut region 1002 (FIG. 21), thereby providing a means to secure the rigid needle shield 10 to the syringe 1000.

After being fully assembled to a syringe 1000, to activate the rigid needle shield 10 a user grasps the rigid needle shield 10 about the elongated flexible members 20 to deflect and move the elongated flexible members 20 from the first relaxed position inwardly to a second flexed position, as shown in FIG. 3. Owing to the convex configuration of the middle portion 26, upon the elongated flexible member 20 being deflected to the second flex position, the second end 24 extends beyond the open proximal end 36 of the rigid needle shield 10. The extension of the second end 24 causes the second end 24 to engage at least one of the needle hub 1001 and the shoulder 1005 of the syringe 1000, to thereby move the rigid needle shield 10 distally relative to the syringe 1000. In other words, the rigid needle shield 10 generates a mechanical force sufficient to overcome the initial pull off force of the rigid needle shield 10 from the syringe 1000 and shift the rigid needle shield 10 distally relative to the syringe 1000. Thus, after activation of the rigid needle shield 10, a user will no longer be required to apply any significant tensile force on the rigid needle shield 10 to overcome the initial pull off force, as required in conventional rigid needle shield devices. Some of the normal forces applied to the shield's sidewall to generate the tensile force is converted into a thrust force by the elongated flexible members 20 pushing the shield 10 away from the syringe 1000.

Due to the living hinge connection, a leaf spring connection or other suitable connection of the first end 22 to one of the closed distal end 14 and sidewall 16, the elongated flexible member 20 is biased to extend radially outwardly from the elongated chamber 18. However, when the second end 24 of the elongated flexible member 20 is assembled to the inner portion 30 of the rigid needle shield 10, upon deflection of the elongated flexible member 20, the second end 24 slidingly engages with an inner surface of the inner portion 30 of the rigid needle shield 10 proximate the open proximal end 12.

FIGS. 4-6 illustrate a second preferred embodiment of a rigid needle shield 100 in accordance with the present invention. The rigid needle shield 100 is configured substantially the same as the rigid needle shield 10, except for the number of elongated flexible members 120 and the number of openings 132 about the elongated chamber 118. The rigid needle shield 100 includes four circumferentially and equally spaced apart elongated flexible members 120 and openings 132, as best shown in FIGS. 4 and 5. That is, as shown in FIG. 5, the elongated flexible members 120 are circumferentially spaced apart about ninety degrees from each other. The configuration of the four circumferentially spaced apart elongated flexible members 120 advantageously allows a user to more easily grasp diametrically opposed elongated flexible members 120 to activate the rigid needle shield 100, as shown in FIG. 6.

Figure 7:
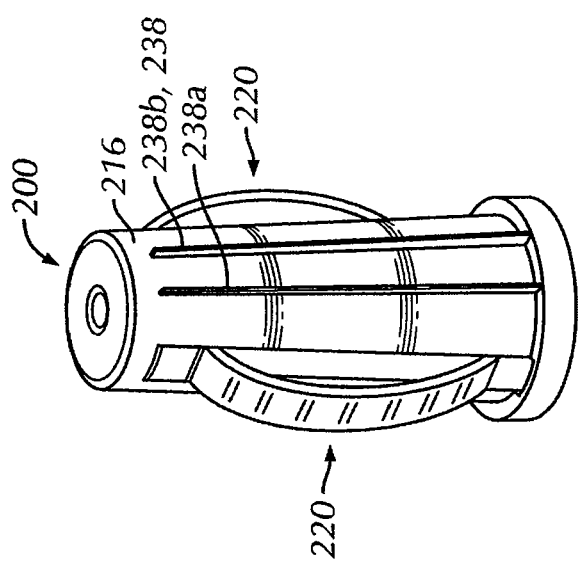
FIG. 7 is a perspective view of a third preferred embodiment of a rigid needle shield in accordance with the present invention.

FIG. 7 illustrates a third preferred embodiment of a rigid needle shield 200. The rigid needle shield 200 is configured substantially the same as the rigid needle shield 10, except for the inclusion of an elongated protrusion 238. The elongated protrusion is configured, as best shown in FIG. 7 having a substantially planar fin-like configuration extending radially outwardly and lengthwise in the axial direction of the sidewall 216 of the rigid needle shield 200. Preferably, the rigid needle shield 200 includes two elongated protrusions 238a, 238b that are diametrically spaced apart. The elongated protrusions 238a, 238b are also configured to taper in the distal direction such that the elongated protrusions 238a, 238b extend further radially outwardly about a proximal region of the rigid needle shield 200 than about a distal region of the rigid needle shield 200. Furthermore, the elongated protrusions 238a, 238b are each circumferentially spaced apart from the elongated flexible members 220 about seventy degrees to one hundred and ten degrees.

FIG. 8 illustrates a fourth preferred embodiment of a rigid needle shield 300 in accordance with the present invention. The rigid needle shield 300 is configured substantially the same as the rigid needle shield 200, except for the configuration of its elongated protrusions 338. The protrusions 338 of the rigid needle shield 300 are each configured substantially as a triangular prism that extends radially outwardly from the elongated chambers sidewall 316 and lengthwise in the axial direction of the elongated chamber 318. The protrusions 338 also taper radially inwardly in the distal direction and are each positioned circumferentially spaced apart from the elongated flexible members 320 about eighty to one hundred degrees, and preferably about ninety degrees.

Figure 9:
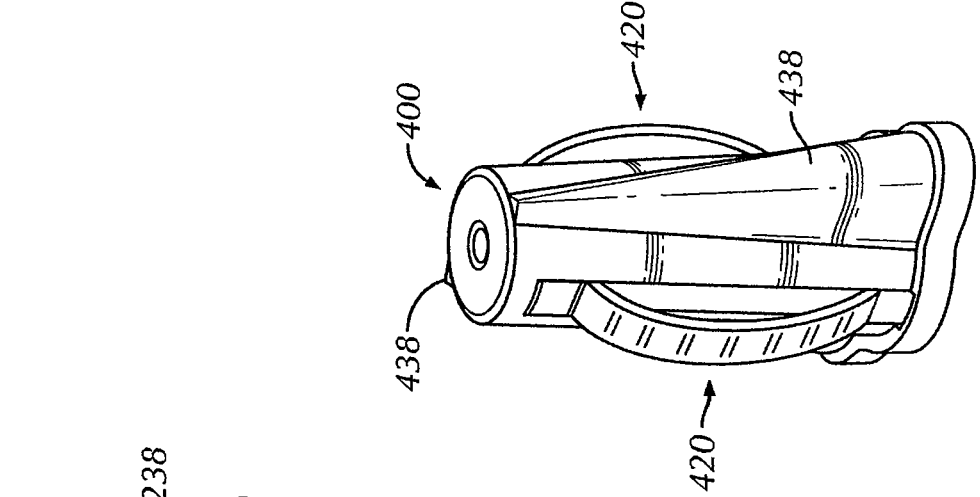
FIG. 9 is a perspective view of a fifth preferred embodiment of a rigid needle shield in accordance with the present invention.

FIG. 9 illustrates a fifth preferred embodiment of a rigid needle shield 400 in accordance with the present invention. The rigid needle shield 400 is configured substantially the same as the rigid needle shield 300, except for the shape of its elongated protrusions 438. The elongated protrusions 438 are each configured as a substantially oblong protrusion that tapers in the distal direction of the rigid needle shield 400. Furthermore, similar to the elongated protrusions 338 of the rigid needle shield 300, the elongated protrusions 438 are each positioned circumferentially spaced apart from the elongated flexible members 420 about eighty to one hundred degrees, and preferably about ninety degrees.

In operation, the elongated protrusions (238, 338, 438) of the rigid needle shield (200, 300, 400) advantageously provides a feature to direct a user to grasp the elongated flexible members (220, 320, 420) for activating the rigid needle shield. In other words, the elongated protrusions (238, 338, 438) serve to direct a user's fingers away from the positions of the protrusions and to the location of the diametrically opposed elongated flexible members (220, 320, 420).

Figure 11:
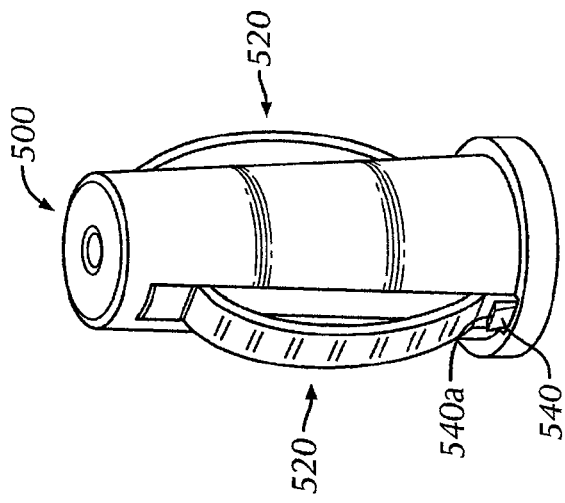
FIG. 11 is a perspective view of the rigid needle shield of FIG. 10 in a fully assembled position.
Figure 10:
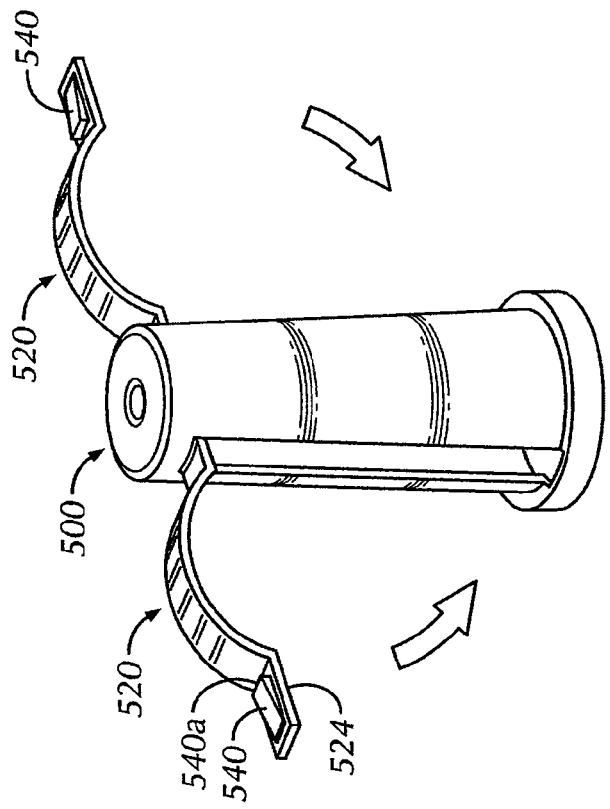
FIG. 10 is a perspective view of a sixth preferred embodiment of a rigid needle shield in accordance with the present invention in an "as molded" position.
Figure 12:
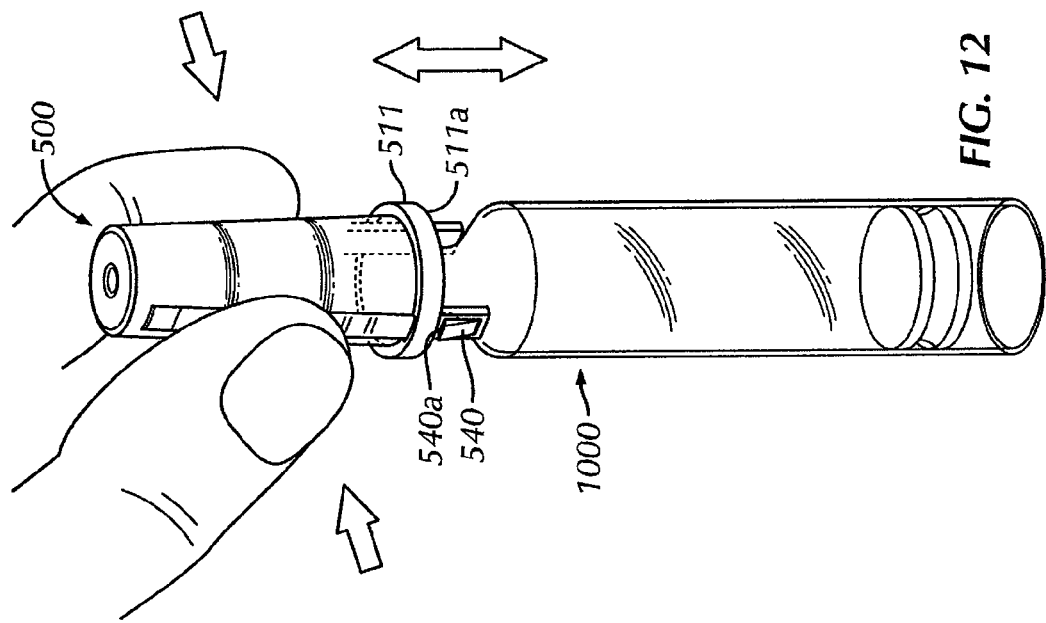
FIG. 12 is a perspective view of the rigid needle shield of FIG. 10 assembled to a syringe in a flexed position.

FIGS. 10-12 illustrate a sixth preferred embodiment of a rigid needle shield 500 in accordance with the present invention. The rigid needle shield 500 is configured substantially the same as the rigid needle shield 10, except for the inclusion of a tab 540 extending from the second end 524 of the elongated flexible member 520. The tab 540 is configured substantially as shown in FIG. 10 having a wedge shape. The wedge shape is positioned about the second end 524 such that the wedge tapers down or inwardly in the proximal direction.

In operation, as the rigid needle shield 500 is activated to remove the rigid needle shield 500 from the syringe 1000, as shown in FIG. 12, the tabs 540 of each elongated flexible member 520 is extended beyond the distal end of the rim 511. Thus, after actuating the rigid needle shield 500 by deflecting the elongated flexible members 540 to its second flexed position, the tabs 540 prevent the elongated flexible members 540 from returning to their first relaxed position. The tabs 540 maintain the elongated flexible members 520 in an extended position by engagement of the wedge's distally facing end surface 540a with a proximally facing surface 511a of the rim 511. In other words, the tab 540 engages the proximal surface 511a of the open proximal end to lock the elongated flexible member 520 in the flexed position. Thus, the tabs 540 provide an anti-recapping feature to prevent a user from recapping the syringe 1000 with the rigid needle shield 500. Since the elongated flexible members 520 remain in the extended position, it prevents the rigid needle shield 500 from reengaging the undercut 1002 (FIG. 21) of the syringe 1000 for retaining the rigid needle shield 500 thereon.

Figure 13:
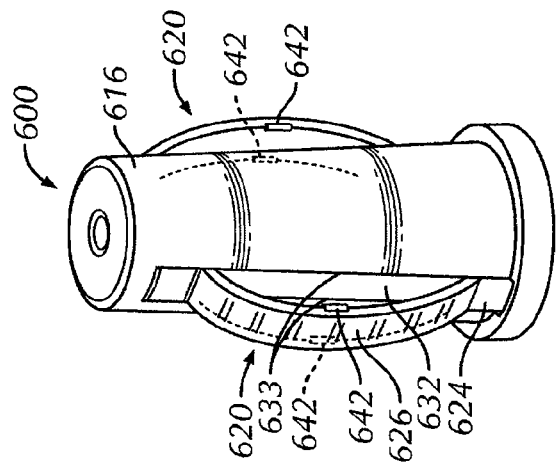
FIG. 13 is a perspective view of a seventh preferred embodiment of a rigid needle shield in accordance with the present invention.

FIG. 13 illustrates a seventh preferred embodiment of a rigid needle shield 600 in accordance with the present invention. The rigid needle shield 600 is configured substantially the same as for the rigid needle shield 100, except for the inclusion of locking tabs 642 on the elongated flexible member 620. The locking tabs 642 are preferably positioned about a mid portion of the middle portion 626 of the elongated flexible member 620. Preferably, the locking tabs 620 are positioned about the lateral sides of the middle portion 626, as best shown in FIG. 13. The locking tabs 624 can be configured as any conventional locking tab or cooperating catches to engage with the sidewall 616, preferably a lateral edge 633 of the opening 632 to lock the middle portion within the opening 632 when the second end 624 is in the second position. Thus, in operation, upon a user deflecting the elongated flexible members 620 to the second flexed position, the locking tabs 642 engage the lateral edges 633 of the sidewall 616 to retain and prevent the elongated flexible members 620 from returning to its initial first relaxed position. In other words, the locking tabs 642 engage with the sidewall 616 to lock the middle portion 626 within the opening 632, when the second end 624 is in the second position. Thus, similar to the tab 540 of the rigid needle shield 500, the rigid needle shield 600 also provides an anti-recapping feature to prevent a user from securing the rigid needle shield 600 back onto a syringe 1000.

FIGS. 14-16 illustrate an eighth preferred embodiment of a rigid needle shield 700, in accordance with the present invention. The rigid needle shield 700 is configured substantially the same as the rigid needle shield 10, except for transverse members 740 on the elongated flexible members 720. The transverse member 740 extends from the lateral sides of the elongated flexible member 720 about a mid portion of the middle portion 726. The transverse member 740 is also configured to extend transversely from the elongated flexible member 720. In addition, the transverse member 740 is configured to have an arc that substantially matches the circumferential profile of the rigid needle shield's elongated sidewall 716. Thus, as shown in FIG. 15, the transverse members 740 of the elongated flexible members 720 substantially circumscribe the elongated chamber 718 of the rigid needle shield 700.

Each transverse member 740 also includes cooperating catches 742 about its lateral edges. The cooperating catches 742 allow opposing transverse members 740 to be secured together in the second flexed position when the rigid needle shield 700 is activated, as shown in FIG. 16, by squeezing the elongated members 720 together. The cooperating catches 742 can be any conventional cooperating catches known in the art, such as snap fits or detents, hooks and undercuts, etc. to hold the elongated flexible members 720 in the second flexed position. Alternatively, the catches 742 can be directed inwardly, towards the concavity of the arc of the transverse member 740, so as to engage an edge of one of a pair of elongated slots or grooves 744, that optionally might be provided for that purpose in the sidewall 716 of the shield 700 at diametric positions between the elongated members 720. Thus, similar to the rigid needle shields 500, 600, the rigid needle shield 700 also provides an anti-recapping feature to prevent the rigid needle shield 700 from being recapped to the syringe 1000 by maintaining the elongated flexible members 720 in the second flexed position, as shown in FIG. 16.

FIGS. 17-20B illustrate a ninth preferred embodiment of a rigid needle shield 800 in accordance with the present invention. The rigid needle shield 800 is similar to the rigid needle shield 10 having diametrically positioned elongated flexible members 820, 821 and cooperating openings 832a, 832b. Shield 800 differs in how the rigid needle shield 800 is releasably attached to a syringe 1000. As best shown in FIG. 17, the rigid needle shield 800 includes an elongated sidewall 816 defining an elongated chamber 818 with closed distal end 814 and a clamp assembly 846 configured to releasably engage an undercut 1002 of the syringe 1000 (FIG. 21).

The clamp assembly 846 includes a first elongated flexible member 820 and a second elongated flexible member 821 for engaging a distal end of a syringe. Each of the first and second elongated flexible members 820, 821 have respective first ends 820a, 821a (not shown) and respective second ends 820b, 821b. The clamp assembly 846 also includes first and second transverse members 819a, 819b. The first transverse member 819a is configured, as substantially shown in FIGS. 20A and 20B. In particular, the first transverse member 819a is a substantially planar member having an aperture 823a extending therethrough for receiving a needle hub of a syringe. The second transverse member 819b is similarly configured as a substantially planar member having an aperture 823b extending therethrough. The first transverse member 819a has an end connected to the second end 820b of the elongated flexible member 820 such that the first transverse member 819a extends radially inwardly from the second end 820b and substantially transverse to a central longitudinal axis 801 of the rigid needle shield 800, as best shown in FIG. 18. The second transverse member 819b has an end connected to the second end 821b of the elongated flexible member 821 such that the second transverse member 819b extends radially inwardly from the second end 821b and substantially transverse to the longitudinal axis of the rigid needle shield 800, as also best shown in FIG. 18. The second transverse member 819b is a substantially planar member having an aperture 823b extending therethrough for receiving the needle hub of the syringe. Each of the first and second elongated flexible members 820, 821 includes a middle portion 820c, 821c, preferably configured as a leaf spring to bias the first and the second transverse members 819a, 819b to the closed position. The middle portions 820c, 821c and second ends 820b, 821b extend outwardly from the sidewall 816.

When the first and second transverse members 819a, 819b are assembled to the elongated flexible members 820, 821, the apertures 823a, 823b overlap to form a through hole 823c for receiving a distal end of the syringe 1000. Furthermore, the first and second transverse members 819a, 819b are slidable relative to each other along a plane substantially perpendicular to a central longitudinal axis 801 of the rigid needle shield 800. Thus, upon radially inwardly compression of the second ends 820b, 821b of the elongated flexible members 820, 821, the clamp assembly 846 can be moved between a closed position (as shown in FIG. 20A) and an open position (as shown in FIG. 20B). In a relaxed position, the elongated flexible members 820, 821 bias the clamp assembly 846 to the closed position due to the deformation of the first and second elongated flexible members 820, 821 being formed to extend radially outwardly from the sidewall 816 of the rigid needle shield 800. The first position corresponds to the closed position in which the first and the second transverse member engage the needle hub of a syringe and the second position corresponds to the open position in which the first and the second transverse members are spaced apart from the needle hub.

As shown in FIGS. 18 and 19, the rigid needle shield 800 is releasably attached to the syringe 1000 by engagement of the clamp assembly 846 onto a needle hub portion 1001 of the syringe 1000. The syringe 1000 (FIG. 21) includes a barrel 1004 having a shoulder 1005, a needle hub 1001 extending from the shoulder 1005, and a needle 1003 extending from the needle hub 1001. The syringe 1000 also includes an undercut region (see e.g., 1002 of FIG. 21) at or near the hub 1001. Thus, the rigid needle shield 800 covers the needle hub 1001 and needle 1003. The hub 1001 passes through the through hole 823c and the clamp assembly 840 is secured to the undercut region 1002 when the clamp assembly 846 is in the relaxed closed position. As shown in FIGS. 18 and 19, the rigid needle shield 800 can optionally include a resilient needle sheath 848 assembled within the elongated chamber 818 that substantially covers a needle of the syringe 1000 and a portion of the needle hub 1001. The resilient needle sheath 848 has an open proximal end 848a, a closed distal end 848b, and a sidewall 848c defining a receptacle therein. When assembled with the resilient needle sheath 848, the clamp assembly 846 can be configured to squeeze or compress the resilient needle sheath 848 inwardly towards the needle hub 1001 to retain the rigid needle shield 800 on the syringe 1000 (see FIG. 19). In use, a user activates the rigid needle shield 800 by compressing the second ends 820b, 821b and moving the clamp assembly 846 from the closed position to the open position, such that the through hole 823c expands to allow the hub 1001 of the syringe 1000 to pass through the first and second transverse members 819a, 819b.

It will be appreciated by those skilled in the art that changes could be made to the embodiments described above without departing from the broad inventive concept thereof. It is to be understood, therefore, that the present invention is not limited to the particular embodiments disclosed, but it is intended to cover modifications within the spirit and scope of the present invention as set forth in the appended claims.

We claim:

1. A rigid needle shield comprising:
   an open proximal end;
   a closed distal end;
   a sidewall extending between the open proximal end and the closed distal end forming an elongated chamber therein; and
   an elongated flexible member having:
      a first end connected to the rigid needle shield,
      a second end slidably connected to the needle shield proximate the open proximal end, and
      a middle portion extending between the first end and the second end, and deflectable to move the elongated flexible member between a first relaxed position and a second flexed position, wherein the second end extends further beyond the open proximal end in the second flexed position;
   wherein the sidewall includes an opening having a distal end and a proximal end, and wherein the first end of the elongated flexible member is connected to the needle shield proximate the distal end of the opening, and the second end of the elongated flexible member is received within the proximal end of the opening.

2. The rigid needle shield of claim 1, wherein the first end is connected to at least one of the closed distal end and the sidewall, and the second end is a free end.

3. The rigid needle shield of claim 2, wherein the second end slidingly engages an inner portion of the rigid needle shield proximate the open proximal end.

4. The rigid needle shield of claim 1, wherein in the first position, the second end is within the elongated chamber.

5. The rigid needle shield of claim 1, wherein the middle portion is convex, bowing outwardly from the sidewall when in the first position.

6. The rigid needle shield of claim 1, wherein the middle portion extends outwardly from the opening.

7. The rigid needle shield of claim 6, wherein the middle portion includes locking tabs that engage with the sidewall to lock the middle portion within the opening when the second end is in the second position.

8. The rigid needle shield of claim 1, wherein the elongated flexible member is one of two elongated flexible members diametrically opposed from each other.

9. The rigid needle shield of claim 8, wherein each elongated flexible member includes a transverse member having cooperating catches for securing each elongated flexible member to each other in the second position.

10. The rigid needle shield of claim 1, further comprising an elongated protrusion extending from the sidewall circumferentially spaced apart from the elongated flexible member.

11. The rigid needle shield of claim 1, wherein the elongated protrusion is circumferentially spaced apart from the elongated flexible member about 90 degrees.

12. The rigid needle shield of claim 1, wherein the second end of the elongated flexible member includes a tab for engaging a proximal surface of the open proximal end to lock the elongated flexible member in the flexed position.

13. The rigid needle shield of claim 1, wherein the middle portion includes a transverse member having cooperating catches, the sidewall includes a groove, and wherein the cooperating catches engages the groove to secure the transverse member thereto when the elongated flexible member is in the second position.

14. A syringe assembly comprising:
   a syringe that includes:
      a barrel having a shoulder,
      a needle hub extending from the shoulder,
      a needle extending from the needle hub; and
      a rigid needle shield as claimed in claim 1, releasably connected to the needle hub for covering the needle hub and the needle,
   wherein in the first relaxed position, the second end is within the elongated chamber and in moving from the first relaxed position to the second flexed position, the second end extends beyond the open proximal end to engage at least one of the needle hub and the shoulder to move the needle shield distally relative to the syringe.

* * * * *